United States Patent [19]

Wehlage et al.

[11] Patent Number: 5,951,841
[45] Date of Patent: Sep. 14, 1999

[54] ELECTROPLATING BATHS SALTS OF AROMATIC HYDROXY COMPOUNDS AND THEIR USE AS BRIGHTENERS

[75] Inventors: Thomas Wehlage, Speyer; Ulrich Schröder, Frankenthal; Alfred Oftring, Bad Dürkheim, all of Germany

[73] Assignee: BASF Aktiengesellschaft, Ludeigshafen, Germany

[21] Appl. No.: 08/860,301

[22] PCT Filed: Dec. 22, 1995

[86] PCT No.: PCT/EP95/05090

§ 371 Date: Oct. 6, 1997

§ 102(e) Date: Oct. 6, 1997

[87] PCT Pub. No.: WO96/20152

PCT Pub. Date: Jul. 4, 1996

[30] Foreign Application Priority Data

Dec. 23, 1994 [DE] Germany ............... 44 46 329

[51] Int. Cl.⁶ ....................................... C25D 3/00
[52] U.S. Cl. ................. 205/261; 205/253; 205/303; 205/314; 549/287; 558/401; 560/51; 564/123; 568/308
[58] Field of Search ................ 205/253, 302, 205/303, 307, 308, 311, 312, 314, 261; 106/1.05; 549/287; 558/401; 568/308; 560/51; 564/123

[56] References Cited

U.S. PATENT DOCUMENTS

| Re. 27,999 | 4/1974 | Korpiun et al. . | |
|---|---|---|---|
| 3,462,459 | 8/1969 | Jen et al. | 549/287 |
| 3,891,520 | 6/1975 | Todt et al. | 205/314 |
| 4,226,682 | 10/1980 | Popescu | 205/314 |
| 4,229,268 | 10/1980 | Lowery et al. . | |
| 4,242,182 | 12/1980 | Popescu | 205/303 |
| 4,422,908 | 12/1983 | Welch . | |
| 5,421,990 | 6/1995 | Hahn et al. . | |

FOREIGN PATENT DOCUMENTS

| 29 48 261 | 7/1980 | Germany . |
| 41 19 341 | 12/1992 | Germany . |

OTHER PUBLICATIONS

Genshum Sunagawa and Hideo Nakao. "Seven–membered ring compounds, XIII. Reaction of 2–bromo–7methoxytropone with active methylene compounds." Chem. Pharm. Bull. (Tokyo) 13(4), 443–50 (1965). Abstract taken from Chemical Abstracts 63:4274g, 1965.

Koichi Araki, Hironobu Hashimoto, and Juji Yoshimura. "Synthetic Studies on Glycocinnamoylspermidines. Synthesis of a key intermediate of the Diaminohexose moiety."Carbohydr. Res., 109, 143–60 (English). Abstract taken from Chemical Abstracts 98:54363, 1982.

Patent Abstracts of Japan, vol. 14, No. 43 (C–0681), Nov. 6, 1989, Jp 1–275–552, Apr. 28 1988.

*Primary Examiner*—Kathryn Gorgos
*Assistant Examiner*—Wesley A. Nicolas
*Attorney, Agent, or Firm*—Oblon, Spivak, McClelland, Maier & Neustadt, P.C.

[57] ABSTRACT

Salts of aromatic hydroxy compounds are used as brighteners in acidic electroplating baths. Furthermore, acidic electroplating baths for the electrolytic deposition of metallic layers onto shaped articles comprise, as brighteners, at least one novel salt of an aromatic hydroxy compound. Finally, shaped articles are electroplated by a process using the novel acidic electroplating baths.

17 Claims, No Drawings

ELECTROPLATING BATHS SALTS OF AROMATIC HYDROXY COMPOUNDS AND THEIR USE AS BRIGHTENERS

I. SUBJECT MATTER OF THE INVENTION

The present invention relates to salts of aromatic hydroxy compounds and their use as brighteners. The present invention furthermore relates to acidic electroplating baths and a process for electroplating shaped articles.

II. BACKGROUND OF THE INVENTION

In the electrodeposition of metals or alloys, in particular of zinc or tin or zinc alloys or tin alloys, onto metallic substrates, such as shaped metal articles or metallated plastic shaped articles, from aqueous acidic solution, a bright coating is frequently desirable in order to give the electroplated article an advantageous decorative appearance. Thus, in addition to the corrosion-inhibiting effect or an effect which improves the mechanical properties of the shaped article, a decorative effect is often desirable. In order to obtain the desired effects, it is essential that the electroplating baths contain certain assistants, since otherwise the metal coatings being deposited from acidic solution are generally dull and frequently also irregular. A group of such assistants for acidic electroplating baths comprises, for example, conductive salts which are used for improving the conductivity of the baths. Another group of assists comprises the brighteners.

U.S. Pat. No. 3,694,330 (Reissue 27 999) discloses acidic electroplating zinc baths which contain ammonium salts and, as brighteners, aromatic carbonyl compounds. Aromatic carboxylic acids and aromatic aldehydes and ketones are mentioned as the latter. Explicitly mentioned are, inter alia, cinnamic acid, cinnamaldehyde, benzoic acid, benzalacetone and ethyl benzoylacetate.

U.S. Pat. No. 4,222,908 describes acidic electroplating zinc baths which contain sulfamate ions and, as brighteners, aromatic carbonyl compounds. Aromatic aldehydes and ketones are mentioned, including benzalacetone as a preferred substance.

DE-A-29 48 261 describes acidic electroplating zinc baths which may contain ammonium salts and contain, as brighteners, aromatic, carbonyl-containing compounds, such as o-chlorobenzaldehyde, p-chlorobenzaldehyde, o-hydroxybenzaldehyde, aminobenzaldehyde, veratraldehyde, benzylideneacetone (benzalacetone), coumarin, 3,4,5,6-tetrahydrobenzaldehyde, acetophenone, propiophenone, furfurylideneacetone, 3-methoxybenzalacetone, benzaldehyde, vanillin, hydoxybenzaldehyde, anisaldehyde, benzoic acid, sodium benzoate, sodium salicylate or 3-pyridinecarboxylic acid (nicotinic acid). The use of polymeric sulfur-containing compounds of a defined general formula is described here for improving the properties of the electroplating baths.

The most important member of such brighteners for acidic zinc baths is benzylideneacetone (benzalacetone). Owing to its marked vapor pressure, benzylideneacetone can evaporate from electroplating baths, leading to losses of substance. Furthermore, these compounds and their homologs cause allergic reactions in many people who handle them, such as skin disorders and itching. In addition, benzalacetone is not water-soluble and must be solubilized with the aid of, in general, toxic solvents. These solvents frequently have a low flashpoint, necessitating additional safety measures.

DE-A-41 19 341 (2) recommends replacing brighteners based on benzylideneacetone in aqueous acidic electroplating baths for the deposition of zinc or zinc alloys by certain other substances which achieve the efficiency of the known brighteners but do not adversely affect the health of persons who handle these substances. However, the compounds disclosed there have the other disadvantages mentioned above.

It is an object of the present invention to provide compounds as brighteners in aqueous acidic electroplating baths, which compounds achieve the efficiency of the known brighteners, in particular of benzylideneacetone, and have a lower vapor pressure as a single substance and in the electroplating baths, in order to avoid losses of substance. The novel compounds should furthermore be water-soluble so that organic solvent can be dispensed with and the concentration of solubilizers in the elecroplating baths can be reduced.

III. DESCRIPTION OF THE INVENTION

We have found that this object is achieved, according to the invention, by aromatic compounds of the formula I

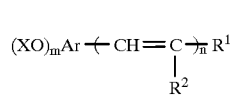
$$(XO)_mAr-(CH=C)_n-R^1 \atop {| \atop R^2}} \qquad (I)$$

where m is an integer $\geq 1$;

n is 0 or 1;

Ar is a phenylene or naphthylene radical which is unsubstituted or substituted by one or more radicals which may be identical or different and are selected from the group consisting of
$C_1$–$C_8$-alkyl,
$C_1$–$C_8$-alkoxy,
$C_1$–$C_4$-alkoxycarbonyl,
halogen,
phenyl and
benzyl radicals;

$R^1$ is cyano or acyl of the formula —$COR^3$, where $R^3$ is a $C_1$–$C_8$-alkyl, $C_2$–$C_8$-alkenyl or $C_2$–$C_8$-alkynyl radical which is unsubstituted or substituted by one or more radicals which may be identical or different and are selected from the group consisting of
$C_1$–$C_4$-alkoxycarbonyl,
$C_1$–$C_4$-alkoxy,
carbonyl and
cyano radicals;
a phenyl or benzyl radical which is unsubstituted or substituted by one or more radicals which may be identical or different and are selected from the group consisting of
$C_1$–$C_4$-alkyl,
$C_1$–$C_4$-alkoxy,
$C_1$–$C_4$-alkoxycarbonyl,
halogen,
hydroxyl and
phenyl radicals;
$C_5$–$C_8$-cycloalkyl;
hydroxyl;
$C_1$–$C_4$-alkoxy or
hydrogen;

$R^2$ is hydrogen,
$C_1$–$C_8$-alkyl,
phenyl,
benzyl,
cyano or
hydroxyl, or a radical of the formula
—COR$^4$,
—COOR$^4$,
—COCH$_2$COOR$^4$,
—OR$^4$ or
—CONR$^4$R$^5$,
where
R$^4$ and R$^5$, which may be identical or different, are each
hydrogen,
C$_1$–C$_8$-alkyl,
phenyl or
benzyl,
and
X is an alkali metal or alkaline earth metal atom or ammonium, with the proviso that the sodium salt of vanillideneacetone and the sodium salt of 5-bromovanillideneacetone are excluded.

We have found that this object is furthermore achieved by compounds of the formula II

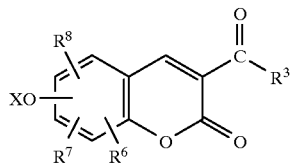

where
R$^6$, R$^7$ and R$^8$, which may be identical or different, are each
hydrogen,
C$_1$–C$_8$-alkyl,
C$_1$–C$_8$-alkoxy,
C$_1$–C$_4$-alkoxycarbonyl,
halogen,
phenyl or
benzyl, or
a radical of the formula —OX, and
R$^3$ and X have the meanings stated in the case of the compounds of the formula I.

The compounds of the formula II may be considered as internal esters (lactones of the corresponding coumarinic acid derivatives) of compounds of the formula I.

The compounds of the formulae I and II are salts of aromatic hydroxy compounds and surprisingly have excellent water solubility. The compounds, both in pure form and in aqueous solution in electroplating baths, furthermore have a lower vapor pressure than the corresponding prior art neutral compounds.

In the compounds of the formulae I and II,
C$_1$–C$_8$-alkyl is methyl, ethyl, n-propyl, isopropyl, n-butyl, isobutyl, tert-butyl, n-pentyl, isopentyl, n-hexyl, isohexyl, n-heptyl, isoheptyl, n-octyl or isooctyl;
C$_1$–C$_8$-alkoxy is methoxy, ethoxy, n-propoxy, isopropoxy, n-butoxy, isobutoxy, tert-butoxy, n-pentyloxy, isopentyloxy, n-hexyloxy, isohexyloxy, n-heptyloxy, isoheptyloxy, n-octyloxy or isooctyloxy;
C$_1$–C$_4$-alkoxycarbonyl is methoxycarbonyl, ethoxycarbonyl, n-propoxycarbonyl, isopropoxycarbonyl, n-butoxycarbonyl, isobutoxycarbonyl or tert-butoxycarbonyl;
halogen is F, Cl, Br or I;
C$_1$–C$_4$-alkoxy is methoxy, ethoxy, n-propoxy, isopropoxy, n-butoxy, isobutoxy or tert-butoxy;
C$_2$–C$_8$-alkenyl is ethenyl, n-propenyl, isopropenyl, n-butenyl, n-pentenyl, n-hexenyl, n-heptenyl or n-octenyl;
C$_2$–C$_8$-alkynyl is ethynyl, propynyl, n-butynyl, n-pentynyl, n-hexynyl, n-heptynyl or n-octynyl;
C$_1$–C$_4$-alkyl is methyl, ethyl, n-propyl, isopropyl, n-butyl, isobutyl or tert-butyl;
alkali metal is Li, Na, K, Rb or Cs and
alkaline earth metal is Mg, Ca, Sr or Ba.

In the compounds of the formula I in which n is 1,
Ar is preferably phenylene which is unsubstituted or substituted by one or more, in particular one or two, radicals which may be identical or different and are selected from the group consisting of
C$_1$–C$_4$-alkyl, in particular methyl or ethyl;
C$_1$–C$_4$-alkoxy, in particular methoxy or ethoxy
and
Br or Cl;
and/or
R$^1$ is cyano or acyl of the formula —COR$^3$, where
R$^3$ is C$_1$–C$_4$-alkyl, in particular methyl or ethyl, which is unsubstituted or substituted by one or more C$_1$–C$_4$-alkoxy, in particular methoxy or ethoxy, radicals which may be identical or different;
a phenyl or benzyl radical which is unsubstituted or substituted by one or more radicals which may be identical or different and are selected from the group consisting of
C$_1$–C$_4$-alkyl, in particular methyl or ethyl;
C$_1$–C$_4$-alkoxy, in particular methoxy or ethoxy;
hydroxyl or
Br or Cl;
hydroxyl or
C$_1$–C$_4$-alkoxy;
and/or
R$^2$ is preferably hydrogen or a radical of the formula
—COR$^4$;
—COOR$^4$;
—COCH$_2$COOR$^4$ or
—CONR$^4$R$^5$;
where
R$^4$ and R$^5$, which may be identical or different, are each
hydrogen;
C$_1$–C$_4$-alkyl, in particular methyl or ethyl;
phenyl or
benzyl.

In the compounds of the formula I in which n is 0,
Ar is preferably a phenylene or naphthylene radical which is unsubstituted or substituted by one or more, in particular one or two, radicals which may be identical or different and are selected from the group consisting of
C$_1$–C$_4$-alkyl, in particular methyl or ethyl;
C$_1$–C$_4$-alkoxy, in particular methoxy or ethoxy;
halogen, in particular Br or Cl, and
hydroxyl;
and/or
R$^1$ is preferably acyl of the formula —COR$^3$, where
R$^3$ is C$_1$–C$_4$-alkyl which is unsubstituted or substituted by one or more C$_1$–C$_4$-alkoxy, in particular methoxy or ethoxy, radicals which may be identical or different;
a benzyl or phenyl radical which is unsubstituted or substituted by one or more radicals which may be identical or different and are selected from the group consisting of C$_1$–C$_4$-alkyl, in particular methyl or ethyl;

$C_1$–$C_4$-alkoxy, in particular methoxy or ethoxy, and
Br or Cl; or
hydrogen.

In the compounds of the formula II, $R^3$ is preferably $C_1$–$C_4$-alkyl, in particular methyl or ethyl, which is unsubstituted or substituted by one or more $C_1$–$C_4$-alkoxy, in particular methoxy or ethoxy, radicals which may be identical or different;

a phenyl or benzyl radical which is unsubstituted or substituted by one or more radicals which may be identical or different and are selected from the group consisting of $C_1$–$C_4$-alkyl, in particular methyl or ethyl;

$C_1$–$C_4$-alkoxy, in particular methoxy or ethoxy;

hydroxyl or

Br or Cl;

hydroxyl; or $C_1$–$C_4$-alkoxy;

and/or $R^6$, $R^7$ and $R^8$, which may be identical or different, are each preferably hydrogen, $C_1$–$C_4$-alkoxy, in particular methoxy or ethoxy, or a radical of the formula —OX, where X has one of the meanings stated in the case of the compounds of the formula I.

In the compounds of the formula I or II, X is preferably an alkali metal atom, in particular Na or K.

Preferred compounds of the formula I are those in which n is 1;

m is 1;

Ar is phenylene which is unsubstituted or substituted by methoxy or ethoxy;

$R^1$ is cyano or acyl of the formula —$COR^3$, where $R^3$ is methyl or ethyl; methoxy or ethoxy; and $R^2$ is hydrogen, a radical of the formula

—$COR^4$;

—$COOR^4$;

—$CONHR^5$ or

—$CONR^4R^5$, where $R^4$ is methyl or ethyl and $R^5$ is hydrogen;

methyl or ethyl;

phenyl or benzyl;

and

X is Na or K.

Other preferred compounds of the formula I are those in which n is 0;

m is 1;

Ar is a phenylene or naphthylene radical which is unsubstituted or substituted by methyl or ethyl;

methoxy or ethoxy;

$R^1$ is acyl of the formula —$COR^3$, where $R^3$ is hydrogen or phenyl;

and

X is Na or K.

Furthermore, preferred compounds of the formula II are those in which $R^3$ is methoxy or ethoxy;

one of the radicals $R^6$, $R^7$ and $R^8$ is hydrogen or methoxy or ethoxy and the other two radicals are each hydrogen; and X is Na or K.

The hydroxybenzylidene derivatives and hydroxynaphthylidene derivatives used as starting materials for the preparation of the compounds of the formula I (n=1) are obtainable, for example, by an aldol condensation or Knoevenagel condensation of the correspondingly substituted hydroxybenzaldehyde or hydroxynaphthaldehyde compounds with the correspondingly substituted alkyl nitrile or alkyl carbonyl compounds or the correspondingly substituted acylacetic acid or cyanoacetic acid derivatives and their esters and amides. In the synthesis of the benzylideneacetone derivatives, both the E and the Z derivatives are obtained. Corresponding reactions have been described, for example, by Zoeller and Sumner in J. Org. Chem. 55 (1990), 319–324.

The o-hydroxybenzophenones used as starting materials for the preparation of compounds of the formula I (n=0) can be prepared, for example, by a Fries arrangement reaction in the usual manner from the correspondingly substituted aryl esters. Corresponding reactions are described, for example, in H. Henecka, Houben-Weyl, Methoden der organischen Chemie, Vol. 7/2a, page 379 et seq., Thieme-Verlag, Stuttgart 1973.

The hydroxycoumarinic derivatives used as starting materials for the preparation of the compounds of the formula II are obtainable by a Knoevenagel condensation of correspondingly substituted hydroxysalicylaldehyde derivatives with correspondingly substituted acetoacetic acid derivatives. Corresponding reactions have been described by van den Goorbergh et al. in Synthesis (1984), 859–860.

The novel salts of the compounds of the formulae I and II can be prepared by reacting the hydroxy derivatives, for example with corresponding alkali metal, alkaline earth metal or ammonium hydroxides. The preparation of the sodium salt of vanillideneacetone and of the sodium salt of 5-bromovanillideneacetone is described, for example, by Glaser and Tramer in J. Prakt. Chem. 116 (1927), 331–346.

The present invention furthermore relates to an acidic electroplating bath for the electrolytic deposition of metallic layers on shaped articles, which comprises one or more metal salts, one or more brighteners, if required one or more conductive salts and, if required, one or more auxiliary brighteners, wherein the bath comprises, as brighteners, at least one of the abovementioned compounds of the formula I or II, the sodium salt of vanillideneacetone and/or the sodium salt of 5-bromovanillideneacetone.

Preferred metal salts are zinc salts and tin salts.

The compounds of the formulae I or II are used in the novel acidic electroplating baths advantageously in an amount of 0.01–3, preferably 0.05–1.5, particularly preferably 0.1–0.7, g/l.

It is also possible to use mixtures of compounds of the formulae I or II as brighteners and to use the brighteners of the formulae I or II together with other known brighteners.

Benzoates, preferably alkali metal or ammonium benzoates, in particular sodium benzoate, in concentrations of 0.1–8, preferably 1–4, g/l, may advantageously be used as additional brighteners.

The novel aqueous acidic electroplating baths have the usual compositions with regard to the other components. They contain, for example, 50–150 g/l of zinc chloride or the equivalent amount of zinc sulfate. If alloys of zinc, for example with cobalt and/or nickel and/or iron, are to be deposited onto metallic shaped articles, the baths additionally contain, as a rule, 1–30 g/l of cobalt sulfate and/or nickel sulfate and/or iron sulfate or the equivalent amount of another, water-soluble cobalt and/or nickel and/or iron salt. It is also possible to use the corresponding tin salts in equivalent amounts.

A further conventional component of the baths comprises conductive salts, in particular sodium salts, potassium salts and ammonium salts. A suitable conductive salt is potassium chloride, which is usually present in a concentration of 100–250 g/l in a novel electroplating bath. Other conductive salts are, for example, ammonium chloride and sodium chloride, which are usually used in a concentration of 10–150 g/l A further conventional component of the novel aqueous acidic electroplating baths comprises surfactants or wetting agents, in particular nonionic and ionic surfactants, which act as auxiliary brighteners. Suitable nonionic surfactants are disclosed, for example, in British Patent 1,149,106. These are adducts of ethylene oxide with fatty alcohols, for example with $C_8$–$C_{18}$-alcohols, or adducts of ethylene oxide with phenol or alkylphenols, in particular with nonylphenol. As a rule, 5–100 mol of ethylene oxide are subjected to an addition reaction per mole of alcohol or phenol. Polyoxyalkylated naphthols may also be added.

Further useful nonionic surfactants include poly (alkyleneimines). Poly(alkyleneimines) may be used as such or they may be reacted with a cyclic carbonate which consists of carbon, hydrogen and oxygen atoms. A description of the preparation of such compounds is disclosed in U.S. Pat. No. 2,824,857.

Suitable anionic surfactants are disclosed, for example, in U.S. Pat. No. 3,787,296. These are mainly sulfated polyethers, which are obtainable, for example, by an addition reaction of ethylene oxide with fatty alcohols, fatty amines, amides of $C_6$–$C_{10}$-carboxylic acids and relatively long-chain fatty acids and a subsequent sulfonation in each case. Sulfonates of polyalkylene oxides or block copolymers of ethylene oxide and propylene oxide are also used as anionic surfactants.

A further group of anionic surfactants is disclosed in EP-B-115 020. Sulfonated and sulfatedalkylphenolethoxyl of the general formula

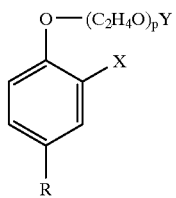

where R is $C_4$–$C_{20}$-alkyl, X and Y are each a radical of the formula —$SO_3H$ or —$SO_3Me$ and Me is ammonium, an alkali metal or one equivalent of an alkaline earth metal or zinc atom and p is 5–50, are described.

In addition to such compounds, other suitable anionic surfactants are the sulfonated and sulfated products whose polyether chain contains 1–25 propylene oxide or butylene oxide units.

DE-C-38 39 824 discloses anionic additives based on monobasic and polybasic ethersulfonic acids. These are prepared by individual or combined sulfopropylation and/or sulfobutylation of the following hydroxyl-containing compounds:

a) block polymers of ethylene oxide and/or glycidol with propylene oxide and/or butylene oxide;

b) monohydric or polyhydric saturated or unsaturated aliphatic alcohols and monohydric or polyhydric, alkylated or nonalkylated phenols or naphthols, including their alkoxylates.

The advantage of the sulfonated and sulfated alkylphenol alkoxylates is that they have an extremely high cloud point so that the electrolytic deposition of the metal, in particular of zinc, can be carried out not only at 20–30° C. but also at 30–90° C., preferably 40–50° C.

Further suitable surfactants include phenol/formaldehyde condensates and naphthalenesulfonic acid/formaldehyde condensates.

In addition to the stated surfactants, polyethylene glycols having molecular weights 200–1000 g/mol are also suitable auxiliary brighteners.

The surfactants and other auxiliary brighteners are used in the novel aqueous acidic electroplating baths usually in amounts of 1–20, preferably 2–15, g/l. It is also possible to use a mixture of a plurality of surfactants, or auxiliary brighteners.

The pH of the novel aqueous acidic electroplating baths is, as a rule, 3–7, preferably 4–5. It is established, for example, by adding acids, for example conventional mineral acids, such as sulfuric acid or hydrochloric acid.

The present invention furthermore relates to a process for the electroplating of shaped articles, which comprises 1. bringing a shaped article into contact with a novel acidic electroplating bath and 2. carrying out electroplating.

By means of the novel process, for example, shaped articles comprising metals, mainly comprising iron or steel, arm electroplated in order to protect them from corrosion and simultaneously to give them great brightness. The novel acidic electroplating baths used for this purpose give, with the entire, technically relevant current density range, very bright and ductile metal coatings, for example zinc coatings, the quality of which corresponds or is even superior to the quality of the coatings obtainable using benzylideneacetone according to the prior art.

Synthesis Examples for compounds of the formula are I and II and Use Examples for novel acidic electroplating baths are described below.

IV. EXAMPLES

The subjects of the present invention a illustrated by the following examples, in which further preferred individual feature of the invention are described.

1. Synthesis Examples

Synthesis Examples for some of the novel compounds of the formulae I and II are described below.

Example 1

Preparation of the sodium salt of vanillideneacetone:

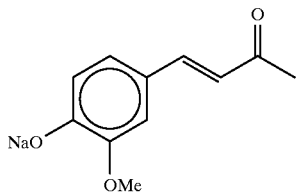

4.9 g (0.032 mol) of vanillin were dissolved in 15 ml of acetone, and 5.3 ml of 50% strength sodium hydroxide solution were added. Thereafter, 10 ml of water were added and stirring was carried out for 20 hours at room temperature. The precipitated residue was washed with acetone and dried. 7 g (corresponding to a yield of 95%) of the title compound were obtained in the form of an orange-yellow solid The purity of the product was >97%.

Example 2

Preparation of the sodium salt of ethylvanillideneacetone:

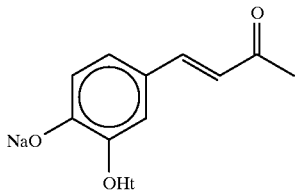

The title compound was prepared similarly to Example 1 from ethylvanillin, sodium hydroxide solution and acetone, in a yield of 95%.

Example 3

Preparation of the potassium salt of 4-hydroxybenzylideneacetone:

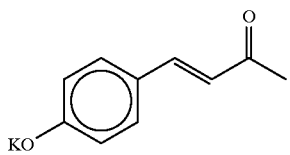

The title compound is prepared similarly to Example 1 from 4-hydroxybenzaldehyde, potassium hydroxide solution and acetone, in a yield of 50%.

Example 4

Preparation of the potassium salt of methyl 4-hydroxybenzalacetoacetate:

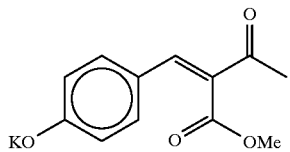

232 g (2 mol) of methyl acetoacetate, 244 g (2 mol) of 4-hydroxybenzaldehyde, 24 g (0.4 mol) of glacial acetic acid and 6.8 g (0.08 mol) of piperidine were dissolved in 459 ml of methylcyclohexane. The reaction solution was heated to the boil, and the water of reaction was separated off for one hour in a water separator. After the solvent had been decanted, the product was taken up in diethyl ether, filtered off with suction and dried. 362 g (corresponding to a yield of 82%) of methyl 4-hydroxybenzalacetoacetate were obtained. 22 g (0.1 mol) of methyl 4-hydroxybenzalacetoacetate were dissolved in 100 ml of methanol, and 5.6 g (0.1 mol) of KOH in 38 g of methanol were added. Stirring was carried out for 2.5 hours at room temperature, after which the reaction mixture was evaporated down and the remaining residue was dried. 25 g (corresponding to a yield of 97% of the title compound were obtained in the form of a red solid. The purity of the product was >95%.

Example 5

Preparation of the potassium salt of N-methyl-4-hydroxybenzalacetoacetamide:

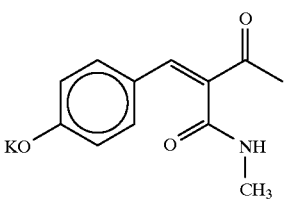

The title compound was prepared similarly to Example 4 from 4-hydroxybenzaldehyde and N-methylacetoacetamide, in a yield of 62%.

Example 6

Preparation of the potassium salt of N-benzyl-4-hydroxybenzalacetoacetamide

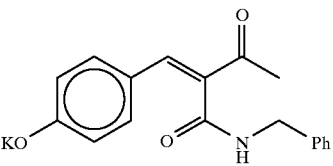

The title compound was prepared similarly to Example 4 from 4-hydroxybenzaldehyde and N-benzylacetoacetamide, in a yield of 83%.

Example 7

Preparation of the potassium salt of methyl 3-hydroxybenzalacetoacetate:

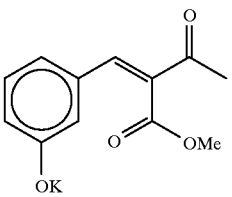

The title compound was prepared similarly to Example 4 from 4-hydroxybenzaldehyde and methyl acetoacetate, in a yield of 43%.

Example 8

Preparation of the potassium salt of methyl vanillideneacetoacetate:

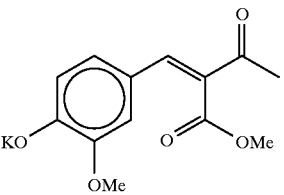

The title compound was prepared similarly to Example 4 from vanillin and methyl acetoacetate, in a yield of 98%.

Example 9

Preparation of the potassium salt of 4-hydroxybenzalacetoacetamide:

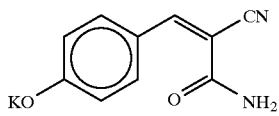

The title compound was prepared similarly to Example 4 from 4-hydroxybenzaldehyde and cyanoacetamide, in a yield of 80%.

Example 10

Preparation of the potassium salt of N-benzyl-2-hydroxybenzalacetoacetamide:

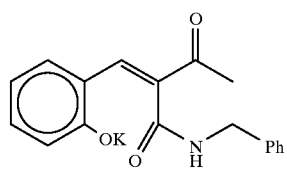

The title compound was prepared similarly to Example 4 from 4-salicylaldehyde and N-benzylacetoacetamide, in a yield of 78%.

Example 11

Preparation of the potassium salt of N-phenyl-4-hydroxybenzalacetoacetamide:

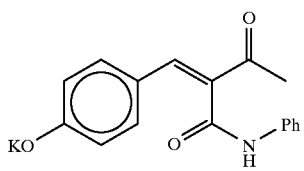

The title compound was prepared similarly to Example 4 from 4-hydroxybenzaldehyde and N-phenylacetoacetamide, in a yield of 98%.

Example 12

Preparation of the potassium salt of dimethyl 3-hydroxybenzalmalonate:

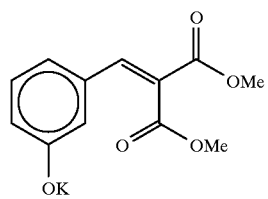

The title compound was prepared similarly to Example 4 from 3-hydroxybenzaldehyde and dimethyl malonate, in a yield of 51%.

Example 13

Preparation of the potassium salt of 7-hydroxy-3-acetylcoumarin:

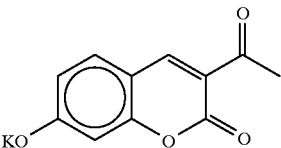

The title compound was prepared similarly to Example 5 from 2,4-dihydroxybenzaldehyde and methyl acetoacetate, in a yield of 42%.

Example 14

Preparation of the potassium salt of ethyl 4-hydroxybenzalacetoacetate:

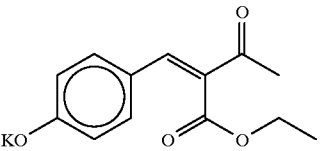

The title compound was prepared similarly to Example 4 from 4-hydroxybenzaldehyde and ethyl acetoacetate, in a yield of 95%.

Example 15

Preparation of the potassium salt of vanillideneacetone:

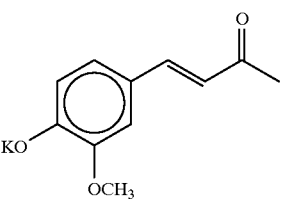

The title compound was prepared similarly to Example 1 from vanillin, acetone and potassium hydroxide, in a yield of 92%.

Example 16

Preparation of the sodium salt of 2-hydroxy-5-methylbenzophenone:

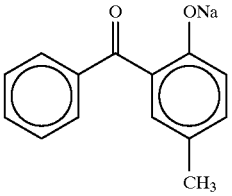

38 g (0.3 mol) of dimethylcyclohexylamine and 27 g (0.25 mol) of p-cresol in 150 ml of chlorobenzene were initially taken. 35.1 g (0.25 mol) of benzoyl chloride were added dropwise over one hour, the temperature increasing to 50° C. After cooling to room temperature, the suspension was added to 100 ml of water in order to separate off the dimethylcyclohexylamine hydrochloride. The organic phase was separated off and was dried by partial distillation. 33 g (0.25 mol) of aluminum trichloride were then added a little at a time at room temperature in the course of 30 minutes. During this procedure, the internal temperature increased to 50° C. The batch was stirred at 130° C. for about 10 hours until the evolution of HCl gas had ceased. After cooling to 60° C., the reaction mixture was poured onto ice water. The phases were separated and the aqueous phase was extracted twice with chlorobenzene. The combined organic phases were dried over magnesium sulfate and then evaporated down. 43 g (corresponding to a yield of 81%) of 2-hydroxy-5-methylbenzophenone were obtained. 25 g (0.12 mol) of the compound were then dissolved in 150 ml of methanol, and 4.1 g of sodium hydroxide in 30 ml of methanol were then added. The refluxing reaction mixture was stirred for 3 hours and then evaporated down in a rotary evaporator. 27 g (corresponding to a yield of 98%) of the title compound were obtained in the form of an orange solid.

Example 17

Preparation of the sodium salt of 2-hydroxy-4-methoxybenzophenone:

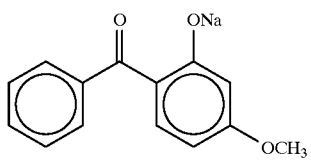

The title compound was prepared similarly to Example 16 from benzoyl chloride and 3-methoxyphenol, in a yield of 70%.

Example 18

Preparation of the sodium salt of 2-hydroxybenzophenone:

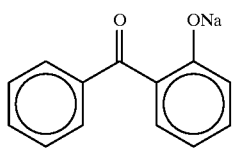

The title compound was prepared similarly to Example 16 from benzoyl chloride and phenol in a yield of 68%.

Example 19

Preparation of the potassium salt of 2-hydroxy-1-naphthaldehyde:

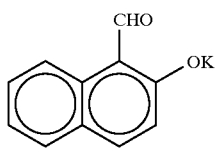

17.2 g of 2-hydroxy-1-naphtaldehyde were dissolved in 100 ml of methanol, and 5.6 g of KOH in 40 ml of methanol were added. The refluxing reaction mixture was stirred for 1.5 hours and then evaporated down. 20 g (corresponding to a yield of 95%) of the title compound were obtained in the form of a dark green solid.

Example 20

Preparation of the potassium salt of 2-hydroxy-5-methylbenzophenone:

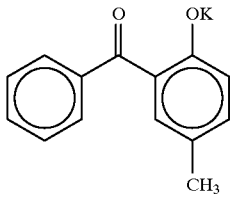

The title compound was prepared similarly to Example 16 from benzoyl chloride, p-cresol and potassium hydroxide solution, in a yield of 72%.

2. Use Examples

The efficiency of brighteners of the formula I or II in an electroplating process is demonstrated using three different aqueous acidic electroplating baths. The brighteners claimed according to the invention were added as 1% strength alkaline aqueous solutions having a pH of 8, preferably 12 (established with NaOH), and the brighteners mentioned in the Comparative Examples were added as a 1% strength methanolic solution.

More highly concentrated solutions may also be used.

Composition of the baths:

Each bath contains, based on 1l of aqueous solution:

| | |
|---|---|
| Zinc chloride | 100 g/l |
| Potassium chloride | 200 g/l |
| Boric acid | 20 g/l |
| Commercial naphthalenesulfonic acid/formaldehyde condensate | 2 g/l |
| Sodium benzoate | 2 g/l |
| Commercial fatty alcohol polyethylene glycol ether having 10 ethylene glycol units | 1 g/l |

Furthermore:

Nonylphenol polyethylene glycol ether, sulfonated and sulfated, having 10 ethylene glycol units

| | |
|---|---|
| Bath 1: | 4 g/l |
| Bath 2: | 10 g/l |
| Bath 3: | 2 g/l | and novel brightener: cf Table I

The pH of the baths was 4.8. The pH was established in each case using dilute hydrochloric acid. The zinc-plating of brass or steel sheets lasted 10 minutes in each case. It was carried out in a 250 ml Hull cell using 1 or 2 amps at the stated temperature. After the zinc-plating, the metal sheet was briefly immersed in 0.5% strength $HNO_3$ solution, after which blue chromatization was carried out.

The quality of the zinc coatings obtained is shown in Table I below. The brightness and ductility of the electroplatings were assessed visually and were given the ratings 1=poor, 2=low, 3=moderate, 4=good and 5=very good.

Table I shows that the effect of the novel compounds of the formula I or II which were used in the electroplating baths is at least equivalent to the effect of prior art comparison compounds.

TABLE I

| Use Example number | Compound from Synthesis Example number | Compound | Concentration [g/l] | Bath No. | Temperature [° C.] | Result Brightness | Ductility |
|---|---|---|---|---|---|---|---|
| 1 | 1 | Sodium salt of vanillideneacetone | 0.5 | 1 | 23 | 4 | 5 |
| 2 | 1 | See Use Example number 1 | 0.5 | 3 | 23 | 4 | 5 |
| 3 | 2 | Sodium salt of ethylvanillideneacetone | 0.3 | 1 | 23 | 4 | 5 |
| 4 | 3 | Potassium salt of 4-hydroxybenzylideneacetone | 0.3 | 2 | 40 | 4 | 5 |
| 5 | 3 | See Use Example number 4 | 0.3 | 1 | 23 | 4 | 5 |
| 6 | 4 | Potassium salt of methyl 4-hydroxybenzalacetoacetate | 0.1 | 1 | 23 | 4 | 5 |
| 7 | 6 | Potassium salt of N-benzyl-4-hydroxybenzalacetoacetamide | 0.1 | 1 | 23 | 4 | 5 |
| 8 | 7 | Potassium salt of methyl 3-hydroxy-benzalacetoacetate | 1.0 | 1 | 23 | 3 | 5 |
| 9 | 8 | Potassium salt of methyl vanillideneacetoacetate | 0.15 | 1 | 23 | 4 | 5 |
| 10 | 13 | Potassium salt of 7-hydroxy-3-acetylcoumarin | 0.5 | 1 | 23 | 4 | 5 |

TABLE II

| Use Example number | Compound from Synthesis Example number | Compound | Concentration [g/l] | Bath No. | Temperature [° C.] | Result Brightness | Ductility |
|---|---|---|---|---|---|---|---|
| 11 | 13 | See Use example number 10 | 0.5 | 2 | 40 | 4 | 5 |
| 12 | 19 | Potassium salt of 2-hydroxy-1-naphthaldehyde | 0.2 | 3 | 23 | 4 | 5 |
| 13 | 17 | Sodium salt of 2-hydroxy-4-methoxybenzophenone | 0.2 | 1 | 23 | 4–5 | 5 |
| 14 | 17 | See Use Example number 13 | 0.5 | 2 | 40 | 4 | 5 |
| 15 | 18 | Sodium salt of 2-hydroxy-benzophenone | 0.2 | 1 | 23 | 4 | 5 |
| 16 | 16 | Sodium salt of 2-hydroxy-5-methyibenzophenone | 0.15 | 1 | 23 | 4 | 5 |
| 17 | 20 | Potassium salt of 2-hydroxy-methylbenzophenone | 0.15 | 1 | 23 | 4 | 5 |
| 18 | 15 | Potassium salt of vanillideneacetone | 0.5 | 1 | 23 | 4 | 5 |
| For comparison: | | | | | | | |
| 19 | | Methyl benzylideneacetoacetate | 0.1 | 1 | 23 | 4 | 5 |
| 20 | | Benzylideneacetone | 0.3 | 1 | 23 | 4 | 5 |
| 21 | | See Use Example number 20 | 0.3 | 2 | 40 | 4 | 5 |

We claim:

1. An acidic electroplating bath for the electrolytic deposition of metallic layers onto shaped articles, comprising one or more metal salts; one or more brighteners; optionally, one or more conductive salts; and, optionally, one or more auxiliary brighteners, wherein the acidic electroplating bath comprises, as the brighteners, at least one compound which is selected from the group consisting of compounds of formula (I) and compounds of formula (II):

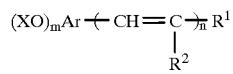
(I)

wherein
m is an integer $\geq 1$;
n is 0 or 1;
Ar is a phenylene or naphthylene radical which is unsubstituted or substituted by one or more radicals which may be identical or different and are selected from the group consisting of
$C_1$–$C_8$-alkyl,
$C_1$–$C_8$-alkoxy
$C_1$–$C_4$-alkoxycarbonyl,
halogen,
phenyl and
benzyl radicals;
$R^1$ is cyano or acyl of the formula —$COR^3$, wherein
$R^3$ is a $C_1$–$C_8$-alkyl, $C_2$–$C_8$-alkenyl or $C_2$–$C_8$-alkynyl radical which is unsubstituted or substituted by one or more radicals which may be identical or different and are selected from the group consisting of $C_1$–$C_4$-alkoxycarbonyl,
$C_1$–$C_4$-alkoxy,
carbonyl and
cyano radicals;
a phenyl or benzyl radical which is unsubstituted or substituted by one or more radicals which may be identical or different and are selected from the group consisting of
$C_1$–$C_4$-alkyl,
$C_1$–$C_4$-alkoxy,
$C_1$–$C_4$-alkoxycarbonyl,
halogen,
hydroxyl and
phenyl radicals;
$C_5$–$C_8$-cycloalkyl;
hydroxyl;
$C_1$–$C_4$-alkoxy or
hydrogen;
$R^2$ is hydrogen,
$C_1$–$C_8$-alkyl,
phenyl,
benzyl,
cyano,
hydroxyl, or
a radical of the formula
—$COR^4$,
—$COOR^4$,
—$COCH_2COOR^4$,
—$OR^4$ or
—$CONR^4R^5$,
wherein,
$R^4$ and $R^5$, which may be identical or different, are each
hydrogen,
$C_1$–$C_8$-alkyl,
phenyl or
benzyl,
and
X is an alkali metal, an alkaline earth metal atom or ammonium;

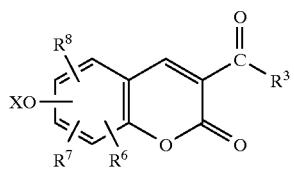

(II)

wherein
$R^6$, $R^7$ and $R^8$, which may be identical or different, are each
hydrogen,
$C_1$–$C_8$-alkyl,
$C_1$–$C_8$-alkoxy,
$C_1$–$C_4$-alkoxycarbonyl,
halogen,
phenyl,
benzyl, or
a radical of the formula —OX; and
$R^3$ and X are as defined above.

2. An acidic electroplating bath as claimed in claim 1, wherein in formula I:
n is 1; and
Ar is phenylene which is unsubstituted or substituted by one or more radicals which may be identical or different and are selected from the group consisting of
$C_1$–$C_4$-alkyl,
$C_1$–$C_4$-alkoxy,
Br and
Cl;
and/or
$R^1$ is cyano or acyl of the formula —$COR^3$, wherein
$R^3$ is $C_1$–$C_4$-alkyl, which is unsubstituted or substituted by one or more $C_1$–$C_4$-alkoxy radicals which may be identical or different;
a phenyl or benzyl radical which is unsubstituted or substituted by one or more radicals which may be identical or different and are selected from the group consisting of
$C_1$–$C_4$-alkyl,
$C_1$–$C_4$-alkoxy,
hydroxy,
Br,
Cl,
hydroxyl; or
$C_1$–$C_4$-alkoxy;
and/or
$R^2$ is hydrogen or a radical of the formula
—$COR^4$,
—$COOR^4$,
—$COCH_2COOR^4$ or
—$CONR^4R^5$,
wherein
$R^4$ and $R^5$, which may be identical or different, are each
hydrogen,
$C_1$–$C_4$-alkyl,
phenyl or
benzyl.

3. An acidic electroplating bath as claimed in claim 1, wherein in formula I:
n is 0; and
Ar is a phenylene or naphthylene radical which is unsubstituted or substituted by one or more radicals which may be identical or different and are selected from the group consisting of
$C_1$–$C_4$-alkyl,
$C_1$–$C_4$-alkoxy,
halogen and
hydroxyl;
and/or
$R^1$ is acyl of the formula —$COR^3$, wherein
$R^3$ is $C_1$–$C_4$-alkyl which is unsubstituted or substituted by one or more $C_1$–$C_4$-alkoxy radicals which may be identical or different;
a benzyl or phenyl radical which is unsubstituted or substituted by one or more radicals which may be identical or different and are selected from the group consisting of
$C_1$–$C_4$-alkyl,
$C_1$–$C_4$-alkoxy,
Br and
Cl; or
hydrogen.

4. An acidic electroplating bath as claimed in claim 1, wherein in formula II:
$R^3$ is $C_1$–$C_4$alkyl, which is unsubstituted or substituted by one or more $C_1$–$C_4$-alkoxy radicals which may be identical or different;
a phenyl or benzyl radical which is unsubstituted or substituted by one or more radicals which may be identical or different and are selected from the group consisting of $C_1$–$C_4$-alkyl,
$C_1$–$C_4$-alkoxy,
hydroxyl,
Br,
Cl
hydroxyl and
$C_1$–$C_4$-alkoxy;
and/or
$R^6$, $R^7$ and $R^8$, which may be identical or different, are each
hydrogen,
$C_1$–$C_4$-alkoxy, or
a radical of the formula —OX, wherein X is as defined in claim 1.

5. An acidic electroplating bath as claimed in claim 1 wherein X is an alkali metal atom.

6. An acidic electroplating bath as claimed in claim 1 wherein in formula I:
n is 1;
m is 1;
Ar is phenylene which is unsubstituted or substituted by methoxy or ethoxy;
$R^1$ is cyano or acyl or the formula —$COR^3$, wherein
$R^3$ is methyl, ethyl, methoxy or ethoxy;
$R^2$ is hydrogen or a radical of the formula
—$COR^4$,
—$COOR^4$,
—$CONHR^5$ or
—$CONR^4R^5$,
wherein
$R^4$ is methyl or ethyl; and
$R^5$ is hydrogen, methyl, ethyl, phenyl or benzyl; and
X is Na or K.

7. An acidic electroplating bath as claimed in claim 1, wherein in formula I:
n is 0;
m is 1;
Ar is a phenylene or naphthylene radical which is unsubstituted or substituted by
methyl, ethyl, methoxy or ethoxy;
$R^1$ is an acyl of the formula —$COR^3$, wherein $R^3$ is hydrogen or phenyl; and
X is Na or K.

8. An acidic electroplating bath as claimed in claim 1, wherein in formula II:
$R^3$ is methoxy or ethoxy;
one of the radicals $R^6$, $R^7$ and $R^8$ is hydrogen, methoxy or ethoxy and the other two radicals are each hydrogen; and
X is Na or K.

9. An acidic electroplating bath as claimed in claim 1, wherein the bath comprises at least one metal salt selected from the group consisting of zinc salts and tin salts.

10. An acidic electroplating bath as claimed in claim 1, wherein the bath comprises at least one conductive salt selected from the group consisting of sodium salts, potassium salts and ammonium salts.

11. An acidic electroplating bath as claimed in claim 1, wherein the bath further comprises at least one auxiliary which is a surfactant.

12. An acidic electroplating bath as claimed in claim 1, wherein the bath comprises at least one additional brightener which is a benzoate.

13. An acidic electroplating bath as claimed in claim 1, wherein the brightener of the formula (I) or (II) is present in a concentration of 0.01–3 g/l.

14. An acidic electroplating bath as claimed in claim 1, wherein the bath has a pH of 3 to 7.

15. A process for the electroplating of shaped articles, comprising electroplating a shaped article in contact with the acidic electroplating bath as claimed in claim 1.

16. A compound of the formula (I):

$$(XO)_mAr{-}(CH{=}C)_n{-}R^1$$
$$\phantom{(XO)_mAr{-}(CH{=}}|$$
$$\phantom{(XO)_mAr{-}(CH{=}C)_n{-}}R^2$$

wherein
n is 1;
m is 1;
Ar is phenylene which is unsubstituted or substituted by methoxy or ethoxy;
$R^1$ is an or acyl of the formula —$COR^3$, wherein
$R^3$ is methyl, ethyl, methoxy or ethoxy;
$R^2$ is a radical of the formula
—$COR^4$,
—$COOR^4$,
—$CONHR^5$ or
—$CONR^4R^5$,
wherein
$R^4$ is methyl or ethyl; and
$R^5$ is hydrogen, methyl, ethyl, phenyl or benzyl; and
X is Na or K, with the proviso that the sodium salt of vanillideneacetone and the sodium salt of 5-bromovanillideneacetone are excluded.

17. A compound of formula (II):

wherein
$R^6$, $R^7$ and R8, which may be identical or different, are each
hydrogen,
$C_1$–$C_8$-alkoxy,
$C_1$–$C_4$-alkoxycarbonyl,
halogen,
phenyl,
benzyl, or
a radical of the formula —OX;
$R^3$ is a $C_1$–$C_8$-alkyl, $C_2$–$C_8$-alkenyl or $C_2$–$C_8$-alkynyl radical which is unsubstituted or substituted by one or more radicals which may be identical or different and are selected from the group consisting of
$C_1$–$C_4$-alkoxycarbonyl,
$C_1$–$C_4$-alkoxy,
carbonyl and
cyano radicals;
a phenyl or benzyl radical which is unsubstituted or substituted by one or more radicals which may be identical or different and are selected from the group consisting of
$C_1$–$C_4$-alkyl,
$C_1$–$C_4$-alkoxy, $C_1$–$C_4$-alkoxycarbonyl,
halogen,
hydroxyl and
phenyl radicals;
$C_5$–$C_8$-cycloalkyl;
hydroxyl;

$C_1$–$C_4$-alkoxy or
hydrogen; and
X is an alkali metal, an alkaline earth metal atom or ammonium.

* * * * *

UNITED STATES PATENT AND TRADEMARK OFFICE
CERTIFICATE OF CORRECTION

PATENT NO. : 5,951,841

DATED : September 14, 1999

INVENTOR(S): Thomas WEHLAGE, et al.

It is certified that an error appears in the above-identified patent and that said Letters Patent is hereby corrected as shown below:

On the title page, item [73], the assignee's city should be:

--Ludwigshafen--

Signed and Sealed this

Twenty-seventh Day of March, 2001

*Attest:*

NICHOLAS P. GODICI

*Attesting Officer*       *Acting Director of the United States Patent and Trademark Office*